(12) United States Patent
Lygin et al.

(10) Patent No.: US 10,906,025 B2
(45) Date of Patent: Feb. 2, 2021

(54) GOLD-BASED CATALYST FOR OXIDATIVE ESTERIFICATION OF ALDEHYDES TO CARBOXYLIC ACID ESTERS

(71) Applicant: Roehm GmbH, Darmstadt (DE)

(72) Inventors: Alexander Lygin, Griesheim (DE); Steffen Krill, Muehltal (DE); Matthias Groemping, Darmstadt (DE); Andreas Tepperis, Bad Koenig (DE)

(73) Assignee: Roehm GmbH, Darmstadt (DE)

( * ) Notice: Subject to any disclaimer, the term of this patent is extended or adjusted under 35 U.S.C. 154(b) by 45 days.

(21) Appl. No.: 15/776,837

(22) PCT Filed: Nov. 11, 2016

(86) PCT No.: PCT/EP2016/077377
§ 371 (c)(1),
(2) Date: May 17, 2018

(87) PCT Pub. No.: WO2017/084969
PCT Pub. Date: May 26, 2017

(65) Prior Publication Data
US 2018/0326400 A1    Nov. 15, 2018

(30) Foreign Application Priority Data
Nov. 19, 2015   (EP) .................................... 15195303

(51) Int. Cl.
*C07C 67/39*   (2006.01)
*B01J 37/02*   (2006.01)
(Continued)

(52) U.S. Cl.
CPC ............... *B01J 21/04* (2013.01); *B01J 21/08* (2013.01); *B01J 21/10* (2013.01); *B01J 23/52* (2013.01);
(Continued)

(58) Field of Classification Search
CPC ... B01J 21/04; B01J 21/08; B01J 21/10; B01J 21/12; B01J 23/52; B01J 23/8906;
(Continued)

(56) References Cited

U.S. PATENT DOCUMENTS

| 5,969,178 A | 10/1999 | Okamoto et al. |
| 6,040,472 A | 3/2000 | Yamamatsu et al. |

(Continued)

FOREIGN PATENT DOCUMENTS

| EP | 1393800 A1 | 3/2004 |
| EP | 2210664 A1 | 7/2010 |

(Continued)

OTHER PUBLICATIONS

International Search Report dated Feb. 20, 2017, in PCT/EP2016/077377, filed Nov. 11, 2016.

(Continued)

*Primary Examiner* — Cam N. Nguyen
(74) *Attorney, Agent, or Firm* — Oblon, McClelland, Maier & Neustadt, L.L.P.

(57) ABSTRACT

The present invention relates to novel catalysts for oxidative esterification, by means of which, for example, (meth) acrolein can be converted to methyl (meth)acrylate. The catalysts of the invention are especially notable for high mechanical and chemical stability even over very long periods. This especially relates to an improvement in the catalyst service life, activity and selectivity over prior art catalysts which lose activity and/or selectivity relatively quickly in continuous operation in media having even a small water content.

20 Claims, 2 Drawing Sheets

Figure 1:
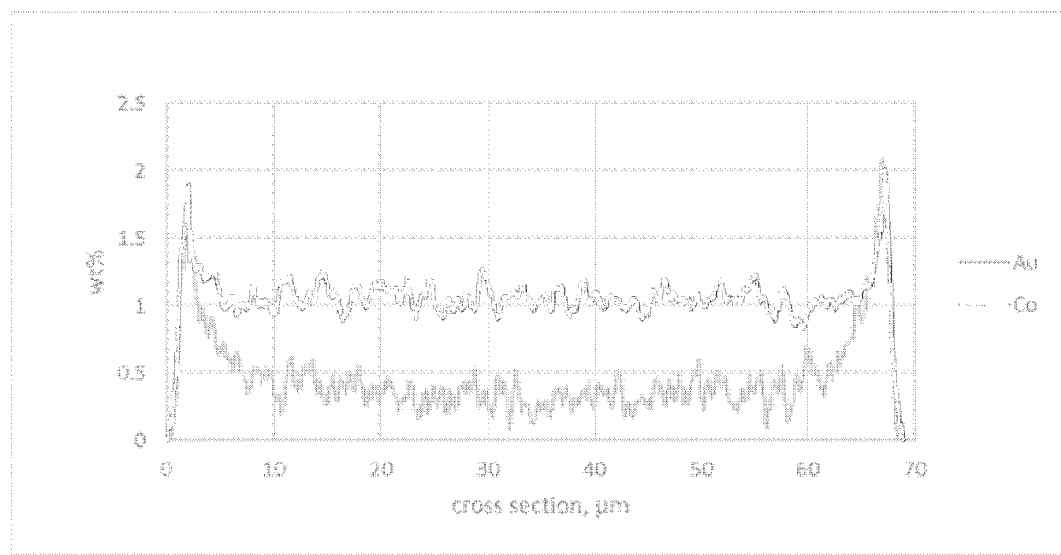

(51) Int. Cl.

| | | |
|---|---|---|
| *B01J 37/06* | (2006.01) | |
| *B01J 37/08* | (2006.01) | |
| *B01J 37/12* | (2006.01) | |
| *B01J 37/14* | (2006.01) | |
| *B01J 21/04* | (2006.01) | |
| *B01J 21/08* | (2006.01) | |
| *B01J 21/10* | (2006.01) | |
| *B01J 21/12* | (2006.01) | |
| *B01J 23/52* | (2006.01) | |
| *B01J 23/89* | (2006.01) | |
| *B01J 35/00* | (2006.01) | |
| *B01J 35/02* | (2006.01) | |
| *B01J 35/10* | (2006.01) | |
| *C07C 67/42* | (2006.01) | |
| *C07C 69/54* | (2006.01) | |

(52) U.S. Cl.
CPC ....... *B01J 23/8906* (2013.01); *B01J 23/8913* (2013.01); *B01J 35/006* (2013.01); *B01J 35/008* (2013.01); *B01J 35/0066* (2013.01); *B01J 35/023* (2013.01); *B01J 35/1019* (2013.01); *B01J 35/1057* (2013.01); *B01J 35/1061* (2013.01); *B01J 37/0201* (2013.01); *B01J 37/024* (2013.01); *B01J 37/0205* (2013.01); *B01J 37/0207* (2013.01); *B01J 37/0211* (2013.01); *B01J 37/06* (2013.01); *B01J 37/08* (2013.01); *B01J 37/12* (2013.01); *B01J 37/14* (2013.01); *C07C 67/39* (2013.01); *B01J 2231/49* (2013.01); *B01J 2523/19* (2013.01); *B01J 2523/27* (2013.01); *B01J 2523/842* (2013.01); *B01J 2523/845* (2013.01); *C07C 67/42* (2013.01); *C07C 69/54* (2013.01)

(58) Field of Classification Search
CPC .. B01J 23/8913; B01J 35/006; B01J 35/0066; B01J 35/008; B01J 35/023; B01J 35/1019; B01J 35/1057; B01J 35/1061; B01J 37/0201; B01J 37/0205; B01J 37/0207; B01J 37/0211; B01J 37/024; B01J 37/06; B01J 37/08; B01J 37/12; B01J 37/14; C07C 67/39
See application file for complete search history.

(56) References Cited

U.S. PATENT DOCUMENTS

| | | | |
|---|---|---|---|
| 7,012,039 B2 | 3/2006 | Watanabe et al. | |
| 9,120,085 B2* | 9/2015 | Suzuki | B01J 21/08 |
| 9,266,091 B2* | 2/2016 | Serban | B01J 23/58 |
| 9,480,973 B2* | 11/2016 | Suzuki | B01J 21/08 |
| 2010/0249448 A1 | 9/2010 | Suzuki et al. | |
| 2011/0184206 A1 | 7/2011 | Suzuki et al. | |
| 2013/0172599 A1 | 7/2013 | Suzuki et al. | |
| 2015/0321178 A1 | 11/2015 | Suzuki et al. | |
| 2016/0251301 A1 | 9/2016 | Krill et al. | |

FOREIGN PATENT DOCUMENTS

| | | |
|---|---|---|
| EP | 2177267 B1 | 7/2013 |
| EP | 2886528 A1 | 6/2015 |

OTHER PUBLICATIONS

Haruta, M. et al. "Low-Temperature Oxidation of CO over Gold Supported on $TiO_2$, alpha-$Fe_2O_3$, and $Co_3O_4$", Journal of Catalysis, vol. 144, 1993, pp. 175-192.

* cited by examiner

GOLD-BASED CATALYST FOR OXIDATIVE ESTERIFICATION OF ALDEHYDES TO CARBOXYLIC ACID ESTERS

FIELD OF THE INVENTION

The present invention relates to novel catalysts for oxidative esterification, by means of which, for example, (meth)acrolein can be converted to methyl (meth)acrylate. The catalysts of the invention are especially notable for high mechanical and chemical stability and for good catalytic performance even over very long periods. This especially relates to an improvement in the catalyst service life, activity and selectivity over prior art catalysts which lose activity and/or selectivity relatively quickly in continuous operation in media having even a small water content.

PRIOR ART

The catalytic oxidative esterification of aldehydes for preparation of carboxylic esters is described extensively in the prior art. For example, it is possible in this way to prepare methyl methacrylate very efficiently from methacrolein (MAL) and methanol. U.S. Pat. Nos. 5,969,178 and 7,012,039 in particular describe a process for continuously preparing MMA from isobutene or tert-butanol. This process has the following steps: 1) oxidation of isobutene or tert-butanol to methacrolein and 2) direct oxidative esterification of MAL with methanol to give MMA with a Pd—Pb catalyst on an oxidic support.

However, all the catalysts known from the prior art have a relevant loss of selectivity and/or activity over the course of prolonged service lives. For example, EP 1 393 800 describes good activities and selectivities, but at the same time no information is given as to the lifetime of the catalysts. Some of these are gold-containing catalysts, the catalytic gold particles described as active oxidation species especially having an average diameter of less than 6 nm. Said gold particles are distributed over a silicon oxide support or a $TiO_2/SiO_2$ support. As additional active components apart from gold, such catalysts also comprise other metals inter alia. The preparation is effected by applying the gold salt and further metal salts to an oxidic support and a subsequent thermal treatment in the presence of hydrogen as reducing agent. For the conversion of pyruvaldehyde to ethyl pyruvate, for example, one catalyst described is a gold- and cobalt-containing catalyst on a $TiO_2$ support. In this catalyst, cobalt is present in metallic form $\{Co(0)\}$. The selectivity for the target product (ethyl pyruvate) in this case is 81% with a space-time yield of 24 mol/kg cat*h. The selectivities of other gold-containing catalysts (without cobalt) for MMA at a content of 4.5% by weight of Au are reported to be up to 93%, and the space-time yield is reported to be up to 50.7 mol of MMA/kg cat*h.

Haruta et al. state, in J. Catal. 1993, Vol. 144, pp 175-192, that gold nanoparticles applied to transition metal oxide supports, such as $TiO_2$, $Fe_2O_3$ or $Co_3O_4$, are active oxidation catalysts. In this case, an interaction between gold and transition metal plays a crucial role for the catalyst activity.

U.S. Pat. No. 6,040,472 describes alternative catalysts, but these lead only to inadequate activities and selectivities for MMA by comparison. In this case, the catalysts are Pd/Pb-containing catalysts having a shell structure. The selectivities for MMA are reported to be up to 91%, and the space-time yield is reported to be up to 5.3 mol.

EP 2 177 267 and EP 2 210 664 describe nickel-containing catalysts with shell structure. Selectivity for MMA in the case of these catalysts is up to 97%. The space-time yield is described as 9.7 mol of MMA/(kg h) with a gold content in the catalyst of about 1% by weight. According to examples, an $NiO_x$/Au catalyst shows much better activities and selectivities for MMA, while other combinations, for example Au with CuO or else $Co_3O_4$, are much less active and selective.

EP 2 177 267 also describes, in comparative example 7, a preparation of Au/$Co_3O_4$-containing catalysts proceeding from cobalt nitrate and auric acid by simultaneous application of Au and Co to an $SiO_2$/MgO support. Experience has shown that this method of application leads to the best results for NiO/Au catalyst. But not in the case of use of cobalt, since the use of the resulting catalyst for preparation of MMA from methacrolein here achieves only 2.6% conversion and 45.8% selectivity at a space-time yield (STY) of 0.3 mol/(kg h). Comparative example 6 of the same patent describes the synthesis and use of an Au/$Fe_3O_4$ catalyst for the same conversion. This catalyst then achieves 10.4% conversion and 55.2% selectivity for MMA at an STY of 1.4 mol/(kg h).

EP 2 210 664 discloses a catalyst having, in the outer region, in the form of what is called an eggshell structure, nickel oxide and gold nanoparticles on a support composed of $SiO_2$, $Al_2O_3$ and a basic element, especially an alkali metal or alkaline earth metal. The nickel oxide is enriched at the surface, but is also present in lower concentrations in deeper layers of the catalyst particle. Such a catalyst exhibits very good activities and selectivities. However, the catalyst produced by the inventive preparation method from this application is relatively sensitive to abrasion and unstable, which is shown by a comparative example later on in the text. As a result, only relatively short service lives are available.

US 2013/0172599, in turn, describes a silicon-containing material consisting of Si, Al and a basic third component, and also a metal having elevated acid resistance as a fourth component. This fourth component is Ni, Co, Zn or Fe, distributed homogeneously in the support. A mixture of Si, Al, the basic element and the fourth component in the production of this material ensures such a homogeneous distribution of this fourth component in the overall support. This material can be used as support for noble metal-containing catalysts. A preferred catalyst variant for the oxidative esterification of methacrolein to MMA includes an Au catalyst supported on an $SiO_2$—$Al_2O_3$—MgO—NiO material.

The overall picture from the prior art is that combinations of gold nanoparticles with other transition metals such as cobalt, zinc or iron, compared to nickel, seem to exhibit only inadequate activities and/or selectivities as catalyst in the synthesis of MMA from methacrolein.

Problem

The primary problem addressed by the present invention was that of providing for the preparation of a novel catalyst for a highly selective oxidative esterification of aldehydes to carboxylic esters. At the same time, this catalyst is to have high mechanical and chemical stability, especially in water- and carboxylic acid-containing mixtures, and is to have a better overall profile of activity, selectivity and lifetime under production conditions compared to the prior art.

A particular problem addressed was that this catalyst is to be suitable for the oxidative esterification of methacrolein to an alkyl methacrylate, especially to MMA.

Further problems which are not stated explicitly may become apparent from the description, the examples, the claims or the overall context of the present invention.

Solution

The stated problems have been solved with the aid of novel catalyst particles for the oxidative esterification of aldehydes to carboxylic esters, especially of methacrolein to MMA.

These inventive catalysts are characterized in that the catalyst particle comprises the elements oxygen, silicon, aluminium, a basic element, gold and at least one element selected from cobalt, iron and zinc, preferably cobalt. Preferably, the gold is in the elemental form of Au{0} and is in the form of nanoparticles. The other elements, by contrast, are in oxidized form (for example in the form of oxides, mixed oxides, solid solutions in one another, etc.). Most preferably, the catalyst particle consists exclusively of gold and the oxides of silicon, of aluminium and of cobalt and of at least one of the basic elements. One example of a particularly suitable composition includes $SiO_2$, $Al_2O_3$, $Co_3O_4$, MgO and Au, especially exclusively these compounds.

In addition, the catalyst particles of the invention are characterized in that the maximum gold concentration or the maximum iron, zinc or cobalt concentration of the catalyst particle is to be found in the outer region thereof. Said outer region makes up a maximum of 60%, preferably a maximum of 40% and more preferably a maximum of 30% of the geometric equivalent diameter of the catalyst particle. In this context, the gold concentration or iron, zinc and/or cobalt concentration in this outer region is at least 1.5 times, preferably at least twice and especially preferably at least 2.5 times as high as the corresponding concentration of these elements in the middle region which makes up the remaining region of the geometric equivalent diameter of the catalyst particle. More preferably, the gold is present to an extent of more than 90% in this outer region.

The determination and analysis of the distribution of the concentrations of gold and/or iron, zinc and/or cobalt across the catalyst particle profile can be effected, for example, by the embedding of the particles into a polymer matrix, subsequent polishing and then SEM-EDX analysis. An analogous analysis method by means of x-ray microanalysis (EPMA) is described, for example, in EP 2 210 664 A1 on page 18.

The basic elements are especially an alkali metal (Li, Na, K, Rb, Cs, Fr), an alkaline earth metal (Be, Mg, Ca, Sr, Ba), a rare earth metal (Sc, Y, La, Ce, Pr, Nd, Pm, Sm, Eu, Gd, Tb, Dy, Ho, Er, Tm, Yb, Lu) or mixtures of these metals. The basic element is generally also present in oxide form.

It has been found that, surprisingly, those catalyst particles of the invention comprising Au and iron, zinc and/or cobalt in the outer region of an eggshell structure solve the above-discussed problems. This is especially true in relation to the retention of a high activity and simultaneously selectivity of the catalyst particle used for the oxidative esterification over a long period. Thus, the catalyst particles of the invention have a particularly good combination of a) low mechanical abrasion of the catalyst particle, b) low leaching of metal ions, which can lead to problems with regard to stability, for example, in the case of iron in an MMA prepared in accordance with the invention, out of the particle and c) long-term retention of catalyst performance with regard to activity and selectivity.

Especially preferred are compositions in which the catalyst particle contains, based on the total molar amount of gold, silicon, aluminium, basic elements and iron, zinc and/or cobalt—i.e. without taking account of further elements, especially of oxygen—0.03 to 3 mol %, preferably 0.1 to 2 mol %, of gold, 40 to 90 mol %, preferably 65 to 85 mol %, of silicon, 3 to 40 mol %, preferably 5 to 30 mol %, of aluminium, 2 to 40 mol %, preferably 5 to 30 mol %, of the basic element and 0.1 to 20 mol %, preferably 0.5 to 15 mol %, of iron, zinc and/or cobalt, where the molar ratio of iron, zinc and cobalt to gold overall is between 0.1 and 20, preferably between 1 and 15. As already detailed, all these elements except for the gold are generally present in the form of oxides.

All proportions, in particular the proportion of basic element, are based on a freshly prepared catalyst. This catalyst may, in a further step, optionally be treated with an acid, such that the proportion of basic element is reduced from the original 2 to 40 mol % to 0.01 to 30 mol %. In addition, such a freshly prepared catalyst, during a process for preparing carboxylic esters, may lose a portion of the basic element. According to the nature of the catalyst, this may lead either to a slight improvement or to a deterioration in the activity and/or selectivity of the process.

The figures listed for the amounts of the elements Si, Al, Au and of the basic elements, and also Fe, Zn and/or Co, are preferably based on 100 mol % of the composition of the catalyst excluding oxygen. This statement of the composition with exclusion of the oxygen present in the oxides is appropriate since some of the elements have distinctly different oxidation states or, for example, mixed oxides may also be present. Preferably, the catalyst except for the oxygen consists of the elements specified.

Preferably, the catalyst particles have a mean geometric equivalent diameter between 1 and 1000 µm, preferably 10 and 250 µm and more preferably between 25 and 200 µm. The thickness of the outer region is preferably between 2 and 100 µm, preferably between 5 and 50 µm. The size of the geometric equivalent diameter is stated because the particles need not necessarily be in entirely spherical form, but may quite possibly also have more complex forms. Preferably, however, the particles are in virtually or ideally spherical form.

It should also be pointed out that the boundary thus contemplated between the core and a shell, moreover, will not be sharp, but may especially be in the form of a gradient with varying composition. For example, the concentration of gold nanoparticles, viewed from the core, may increase from the inside outward. This arises merely from the fact that the particles of the invention generally have porosity.

In the ideal case, an illustrative value of thickness 80 µm of the outer region, for example in the case of a particle having an equivalent diameter of 200 µm, means that, viewed over the diameter, at either outer end thereof, there is 40 µm of outer region with 120 µm of middle region in between. This size was chosen in order to describe the eggshell structure of the catalyst of the invention. The boundary between the outer and inner region can be chosen relatively freely by the person skilled in the art within the ranges specified in the examination of the particles. What is crucial in accordance with the invention is that there is a boundary within the range specified where the conditions exist with regard to the iron, zinc and/or cobalt concentration and the gold concentration. In relation to the iron, zinc and especially the cobalt concentration, this is the inventive core of the present invention.

Preferably, gold and/or gold- and metal oxide-containing, especially cobalt oxide-containing, particles having a mean diameter between 1 and 20 nm, preferably 2 and 10 nm, are present in the outer region of the catalyst particle. According to the production method, it is possible in accordance with the invention that the gold is present either in the form of pure particles or in a mixed form, for example together with the cobalt oxide. In this latter case, the gold is generally mixed only with a portion of the cobalt oxide. In addition, it is optionally also possible in both embodiments that the gold or gold-containing particles, for stabilization, are additionally provided with a thin layer, for example of $SiO_2$ and/or $Al_2O_3$.

Preferably, the catalyst particles of the invention are porous. In this case, the porosity generally does not relate to the gold or gold-containing phases. Such porous catalyst particles have a specific surface area between 100 and 300 $m^2/g$, preferably between 150 and 250 $m^2/g$. In addition, the average pore diameter is generally 1 to 50 nm, preferably 2 to 20 nm.

As well as the catalysts described for an oxidative esterification, another part of the present invention is in particular a process for producing catalysts for an oxidative esterification. This process for producing catalyst particles is characterized in that it has at least the following steps:
1) applying at least one iron, zinc or cobalt compound to a particle consisting of the oxides of silicon, of aluminium and optionally of one or more alkali metals, alkaline earth metals or rare earth metals,
2) optionally and simultaneously preferably partly or fully oxidizing the material from 1) and optionally drying/calcining,
3) applying at least one gold compound to the material from step 2) and
4) drying and/or calcining the material from step 3).

The support particles consisting of the oxides of silicon, of aluminium and optionally of one or more alkali metals, alkaline earth metals or rare earth metals may be prepared, for example, by processes as described in U.S. Pat. No. 6,228,800 B1, page 11 or U.S. Pat. No. 6,040,472, page 27. In this case, silicon, aluminium and optionally alkali metal, alkaline earth metal and rare earth compounds may be mixed successively or simultaneously with one another, preferably as aqueous solutions and/or aqueous suspensions, and the mixture thus prepared can be subjected to at least one thermal treatment. A preferred silicon compound may, for example, be silica sol, i.e. a silicon dioxide nanoparticle dispersion in water. Preferred aluminium, alkali metal, alkaline earth metal or rare earth compounds are, for example, the corresponding water-soluble nitrates or sulphates. When mixing these compounds, the temperature, pH and stirrer speed are set specially. Preferably, the mixing proceeds at a temperature between −20 and 90° C., more preferably between −15 and 50° C. The pH of the mixture can be adjusted by means of addition of a base or acid. Particular preference is given to setting a pH between 0.3 and 2.5 or between 8.0 and 12.0. A preferred stirrer speed is between 50 and 1000 rpm. Thermal treatment is understood to mean partial or complete removal of the water and subsequent or simultaneous breakdown of the thermally labile compounds, for example nitrates, with heating. Preferably, such a thermal treatment is effected in two stages. In a first stage, the mixture of Si, Al and alkali metals/alkaline earth metals/rare earth metals is spray-dried at exit temperature between 95 and 250° C., preferably between 100 and 150° C. In a second stage, the material dried beforehand is calcined at a temperature of 250 to 1000° C., preferably of 280 to 800° C.

With regard to process step 1), the following further aspects arise: The iron, zinc and/or cobalt component, preferably a cobalt component only, can be applied to the support material by impregnation—for example by what is called the incipient wetness impregnation method or other impregnation methods. Preferably, however, the iron, zinc and/or cobalt component is applied from an aqueous solution at a temperature between 50 and 100° C., optimally at a temperature between 70 and 95° C. In addition, the iron, zinc and/or cobalt compound is a water-soluble compound which is added in the form of an aqueous solution. The addition at elevated temperatures simultaneously achieves the positive effect that the structures of the pores in the catalyst particle are positively influenced and hence a more stable particle overall is obtained. On the other hand, it has been found that, surprisingly, the chemical attachment of the iron, zinc and/or cobalt to the support is improved by the higher temperature on addition. Thus, the material losses in an optional wash step are reduced, as is later leaching of metal ions. The described impregnation can also be effected at even higher temperatures, in which case it is necessary to work under pressure for the impregnation process in this process step of the catalyst production.

The oxidation in process step 2) is preferably effected by heating of the particles or of the suspension comprising the particles from process step 1) in the presence of oxygen, for example in the form of air. Alternatively, the oxidation can be effected by adding an oxidizing agent, for example to the suspension. The oxidizing agent may, for example, be $H_2O_2$.

In the oxidation, in particular, Co(II) compounds, for example, are partly or fully oxidized to Co(III). If gold(III) compounds, which are a strong oxidizing agent, are used instead in the presence of Co(II) compounds, there may be unwanted early reduction of gold(III) to metallic gold, which can in turn lead to an inactive or less active oxidation catalyst. Thus, this course of action in particular is less preferred. Process step 2) may optionally include a thermal treatment, for example a further drying and/or calcination, which can be effected before, during or after the application of cobalt.

The preferred oxidation in process step 2 is effected by a calcination in the presence of oxygen at at least 200° C.

Process step 3) is effected by application of at least one gold component, especially in ionic form, to the material from process step 2) and subsequent thermal treatment in process step 4), for example in the form of a calcination. More particularly, the gold is applied with an acidic gold-containing solution generally having a pH between 0.5 and 5, optimally between 1 and 4. Such a solution is produced with auric acid. Preferably, this solution is subsequently partly or fully neutralized, such that the pH of the resulting mixture is between 2 and 8, preferably between 3 and 7. This is effected by adding a base, for example in the form of an NaOH solution. With regard to the variant of base addition, there are again two alternative embodiments:

In the first embodiment, in process step 3), first the basic solution and then the solution comprising auric acid, having a pH between 0.5 and 5, are added to an aqueous suspension of the particles from process step 2).

In the second embodiment, in process step 3), a solution which has been obtained by the partial or complete neutralization of the auric acid solution, previously having had a pH between 0.5 and 5, by the addition of a base, preferably an NaOH solution, is added to an aqueous suspension of the particles from process step 2).

The acidity of the gold-containing solution or the pH of the gold-containing solution has, in particular, a great influence on the formation of various species of gold(III) complex ions in the solution (see, for example, Geochimica et Cosmochimica Acta Vol. 55, pp. 671-676) and ultimately on the nature of the bond to the surface of the support.

Both calcination steps in process steps 2) and 4) are preferably conducted in an oxidizing atmosphere, for example in the presence of atmospheric oxygen. Process steps 1) and 3), and optionally process step 2), are especially conducted in an aqueous medium, especially in an aqueous suspension of the particles.

Preferably, the oxides of silicon, of aluminium and optionally of one or more alkali metals, alkaline earth metals or rare earth metals, within process steps 1) to 3), preferably in or directly after process step 1), are subjected to at least one thermal treatment with water. The water temperature here is between 50 and 100° C., preferably between 70 and 95° C. This thermal treatment achieves the positive effect that the structures of the pores in the catalyst particle are positively influenced and hence a more stable particle overall is obtained.

In a particular but not necessarily preferred variant of this process, the gold-containing solution contains not only the gold compound but at least one additional compound. This compound again includes the elements silicon, aluminium and the basic element(s) of the support material in ionic form. With this variant, an additional protective layer for the gold nanoparticles can arise, which is additionally beneficial for a longer service life of the catalyst. Silicon in ionic form means in this case that silicates, for example sodium silicates or ammonium silicates, which are converted to silicon oxides at a later stage in an optional thermal sintering or calcination, are present in the solution. The other elements in ionic form mean the corresponding water-soluble salts, for example aluminium nitrate, aluminium sulphate, etc.

After the production of the particles described, isolation, for example by means of filtration, and further purification, with particular preference, they are finally calcined in process step 4). This can take place, for example, at temperatures between 200 and 1000° C., more preferably between 250 and 800° C.

It has been found that, surprisingly, this manner of application of gold and iron, zinc and/or cobalt to a previously prepared oxidic support is particularly advantageous. Particular preference is given to this manner of application for the combination of gold and cobalt. This is especially true by comparison with a method known from the prior art in which preparation of the support material is effected from the mixture of Co (Fe, Zn), Si, Al compounds and the salts of basic elements at the same time. This enables preparation of an active and selective catalyst for the oxidative esterification of aldehydes to carboxylic esters, for example of methacrolein to MMA. It appears to be particularly advantageous here that the dried and calcined, porous oxidic support is treated in process step 1 with the solution of a soluble iron, zinc and/or cobalt compound. This has the effect that the iron, zinc and/or cobalt ions preferably cover the surface of the support, including the pore surface in the outer region, and are subsequently fixed thereon by the drying and/or calcining. What is important in this process is the preferred coverage of the pore surface with the iron, zinc and/or cobalt ions—and not the homogeneous distribution thereof, as described in the prior art, particularly in US 2013/0172599. The effect of the combination with the gold which is likewise enriched on the surface of the catalyst particle is that the two catalytically active components Co (Fe, Zn) and Au are better accessible to the reaction medium and can better activate one another, and the catalyst is likewise surprisingly stable and long-lived.

Moreover, it has been found that, surprisingly, as a result of successive application of the iron, zinc and/or cobalt compound and the gold compound, combined with an appropriate oxidative thermal treatment, control transitions between the different oxidation states of gold—typically from $Au^{3+}$ to $Au^0$— and of cobalt—typically from $Co^{2+}$ to $Co^{x+}$ with $2<X\leq3$—proceed at the surface of the oxidic support. For iron, oxidation states of $Fe^{2+}$ to $Fe^{x+}$ with $2<X\leq3$ are typically present. For zinc, only the oxidation state (II) is relevant. Correspondingly, no oxidation of zinc takes place here.

This subsequent redox reaction leads to the more active and selective catalysts compared to the variants known from the prior art (see the comparative examples which follow below).

The combination of these factors enables synthesis of a catalyst with shell structure of the active components (e.g. with Co and Au), having high activity and selectivity and long service lives.

As well as the catalysts described and the process for production thereof described, another part of the present invention is the use of such a catalyst of the invention or catalyst produced in accordance with the invention in the reaction of aldehydes with oxygen and an alcohol to give a carboxylic ester, especially of (meth)acrolein with oxygen and a monofunctional alcohol to give an alkyl (meth) acrylate. The brackets in (meth)acrolein mean that this raw material may be either acrolein or methacrolein. Correspondingly, alkyl (meth)acrylate means either alkyl acrylate or alkyl methacrylate. This alkyl group is determined by the alcohol used.

Preferably, in the case of this use, methacrolein is reacted with oxygen and methanol in the presence of the catalyst of the invention to give MMA.

Alternatively, in the case of this use, it is also possible to react (meth)acrolein with oxygen and a di-, tri- or tetrafunctional alcohol to give a hydroxyalkyl (meth)acrylate and di-, tri- or tetra(meth)acrylate. The latter compounds are known as crosslinkers. A particularly preferred example of a difunctional alcohol is ethylene glycol.

Particular preference is given to conducting the oxidative esterification continuously in the presence of the catalyst of the invention. Most preferably, the catalyst is employed in suspension form (as a slurry) in a stirred reactor during the oxidative esterification.

EXAMPLES

The analysis of the concentration profiles for Co and Au within the catalyst particles is effected by means of the SEM-EDX line scan method. This was done using the following setup:

Microscope: Jeol JSM 7600F; analysis—Oxford AZtec with X-Max 150 detector.

The samples were embedded in a resin and a section was cut with a Leica ultramicrotome with a diamond blade.

The analysis method is based on EDX at acceleration voltage 20 kV. The Co K-alpha peak at 6.924 keV and Au M-alpha peak at 2.120 keV were evaluated.

The examples which follow document the effect mainly for cobalt-containing catalysts. The effect was also shown for Zn-containing catalysts. The results are applicable in a simple manner to catalysts containing iron or mixtures of two or three elements selected from iron, zinc and cobalt.

Example 1 ($SiO_2$—$Al_2O_3$—$MgO$)

A 250 ml beaker is initially charged with 21.36 g of $Mg(NO_3)_2*6H_2O$ and 31.21 g of $Al(NO_3)_3*9H_2O$ together, which are dissolved in 41.85 g of demineralized water while stirring with a magnetic stirrer. Thereafter, 1.57 g of 60% $HNO_3$ are added while stirring. 166.67 g of silica sol (Köstrosol 1530AS from Bad Köstritz, 30% by weight of $SiO_2$, median size of the particles: 15 nm) are weighed into a 500 ml three-neck flask and cooled to 15° C. while stirring. 2.57 g of 60% $HNO_3$ are added gradually to the sol while stirring. At 15° C., the nitrate solution is added to the sol within 45 min while stirring. After the addition, the mixture is heated to 50° C. within 30 min and stirred at this temperature for a further 24 h. After this time, the mixture is spray-dried at exit temperature 130° C. The dried powder (spherical, median particle size 60 μm) is heated in a thin layer in a Naber oven to 300° C. within 2 h, kept at 300° C. for 3 h, heated to 600° C. within 2 h and finally kept at 600° C. for 3 h.

Example 2

A suspension of 10 g of the $SiO_2$—$Al_2O_3$—$MgO$ support from Example 1 in 33.3 g of demineralized water is heated to 90° C. and stirred at this temperature for 15 min. Added to this suspension while stirring is a solution, heated to 90° C. beforehand, of $Co(NO_3)_2*6H_2O$ (569 mg, 1.95 mmol) in 8.3 g of water. After the addition, the mixture was stirred at 90° C. for a further 30 min, then cooled down, filtered at room temperature and finally washed six times with 50 ml each time of water. The material was dried at 105° C. for 10 h, finely crushed with a mortar and pestle, then heated from 18° C. up to 450° C. within 1 h and then calcined at 450° C. for 5 h.

Example 3

A suspension of 15 g of the $SiO_2$—$Al_2O_3$—$MgO$ support from Example 1 in 50 g of demineralized water is heated to 90° C. and stirred at this temperature for 15 min. Added to this suspension while stirring is a solution, heated to 90° C. beforehand, of $CoCl_2$ (697 mg, 2.93 mmol) and LiCl (1.24 g) in 12.5 g of water. After the addition, the mixture was stirred at 90° C. for a further 30 min, then cooled down, filtered at room temperature and finally washed six times with 50 ml each time of water. The material was dried at 105° C. for 10 h, finely crushed with a mortar and pestle, then heated from 18° C. up to 450° C. within 1 h and then calcined at 450° C. for 5 h.

Example 4

A suspension of 10 g of a cobalt-doped $SiO_2$—$Al_2O_3$—$MgO$ support from Example 2 in 33.3 g of demineralized water is heated to 90° C. and stirred at this temperature for 15 min. Added to this suspension while stirring is a solution, heated to 90° C. beforehand, of $HAuCl_4*3H_2O$ (205 mg) in 8.3 g of water. After the addition, the mixture was stirred at 90° C. for a further 30 min, then cooled down, filtered at room temperature and finally washed six times with 50 ml each time of water. The material was dried at 105° C. for 10 h, finely crushed with a mortar and pestle, then heated from 18° C. up to 450° C. within 1 h and then calcined at 450° C. for 5 h.

A line scan SEM-EDX analysis of a cut section of catalyst particles embedded into polymer matrix showed an eggshell distribution for cobalt and for gold in the particle.

Example 5

A suspension of 10 g of a cobalt-doped $SiO_2$—$Al_2O_3$—$MgO$ support from Example 2 in 33.3 g of demineralized water is heated to 90° C. and stirred at this temperature for 15 min. Added to this suspension while stirring is a solution, heated to 90° C. beforehand, of $HAuCl_4*3H_2O$ (205 mg) and 0.52 ml of a one molar NaOH solution (Au/Na=1:1 mol/mol) in 8.3 g of water. After the addition, the mixture is stirred for a further 60 min, then cooled down, filtered at room temperature and finally washed six times with 50 ml each time of water. The material was dried at 105° C. for 10 h, finely crushed with a mortar and pestle, then heated from 18° C. up to 450° C. within 1 h and then calcined at 450° C. for 5 h.

A line scan SEM-EDX analysis of a cut section of catalyst particles embedded into polymer matrix showed an eggshell distribution for cobalt and for gold in the particle.

Example 6

A suspension of 10 g of a cobalt-doped $SiO_2$—$Al_2O_3$—$MgO$ support from Example 2 in 33.3 g of demineralized water is heated to 90° C. and stirred at this temperature for 15 min. This suspension is admixed while stirring with a solution, heated to 90° C. beforehand, of 0.52 ml of a one molar NaOH solution. After stirring at 90° C. for 30 minutes, $HAuCl_4*3H_2O$ (205 mg) in 4.3 g of water is added. After the addition, the mixture was stirred for a further 60 min, then cooled down, filtered at room temperature and finally washed six times with 50 ml each time of water. The material was dried at 105° C. for 10 h, finely crushed with a mortar and pestle, then heated from 18° C. up to 450° C. within 1 h and then calcined at 450° C. for 5 h.

A line scan SEM-EDX analysis of a cut section of catalyst particles embedded into polymer matrix showed an eggshell distribution for cobalt and for gold in the particle.

Example 7

A suspension of 10 g of a cobalt-doped $SiO_2$—$Al_2O_3$—$MgO$ support from Example 3 in 33.3 g of demineralized water is heated to 90° C. and stirred at this temperature for 15 min. Added to this suspension while stirring is a solution, heated to 90° C. beforehand, of $HAuCl_4*3H_2O$ (205 mg) and 0.52 ml of a one molar NaOH solution (Au/Na=1:1 mol/mol) in 8.3 g of water. After the addition, the mixture is stirred for a further 60 min, then cooled down, filtered at room temperature and finally washed six times with 50 ml each time of water. The material was dried at 105° C. for 10 h, finely crushed with a mortar and pestle, then heated from 18° C. up to 450° C. within 1 h and then calcined at 450° C. for 5 h.

A line scan SEM-EDX analysis of a cut section of catalyst particles embedded into polymer matrix showed an eggshell distribution for cobalt and for gold in the particle.

Example 8

A suspension of 10 g of the $SiO_2$—$Al_2O_3$—$MgO$ support from Example 1 in 33.3 g of demineralized water is heated to 90° C. and stirred at this temperature for 15 min. Added to this suspension while stirring is a solution, heated to 90° C. beforehand, of Co(NO$_3$)$_2$*6H$_2$O (569 mg, 1.95 mmol) in 4.2 g of water. After the addition, the mixture was stirred at 90° C. for a further 60 min, in the course of which an air stream is bubbled into the solution. After stirring for 60 minutes, added to this suspension while stirring is a solution, heated to 90° C. beforehand, of HAuCl$_4$*3H$_2$O (205 mg) in 4.2 g of water. After the addition, the mixture was stirred at 90° C. for a further 30 min, then cooled down, filtered at room temperature and subsequently washed six times with 50 ml each time of water. The material was dried at 105° C. for 10 h, finely crushed with a mortar and pestle, heated from 18° C. up to 450° C. within 1 h and calcined at 450° C. for 5 h.

A line scan SEM-EDX analysis of a cut section of catalyst particles embedded into polymer matrix showed an eggshell distribution for Co and for gold.

Example 9

A suspension of 10 g of the SiO$_2$—Al$_2$O$_3$—MgO support from Example 1 in 33.3 g of demineralized water is heated to 90° C. and stirred at this temperature for 15 min. Added to this suspension while stirring is a solution, heated to 90° C. beforehand, of Co(NO$_3$)$_2$*6H$_2$O (569 mg, 1.95 mmol) in 4.2 g of water. After the addition, the mixture was stirred at 90° C. for a further 30 min. H$_2$O$_2$ (30 wt %, 0.45 g) was added dropwise to the mixture. After stirring for a further 60 minutes, added to the suspension while stirring is a solution, heated to 90° C. beforehand, of HAuCl$_4$*3H$_2$O (205 mg) in 4.2 g of water. After the addition, the mixture was stirred at 90° C. for a further 30 min, then cooled down, filtered at room temperature and subsequently washed six times with 50 ml each time of water. The material was dried at 105° C. for 10 h, finely crushed with a mortar and pestle, then heated from 18° C. up to 450° C. within 1 h and calcined at 450° C. for 5 h.

A line scan SEM-EDX analysis of a cut section of catalyst particles embedded into polymer matrix showed an eggshell distribution for Co and for gold.

Example 10

Co(NO$_3$)$_2$*6H$_2$O (569 mg, 1.95 mmol) is dissolved in 5 g of demineralized water and the solution is mixed by vigorous agitation with 10 g of an SiO$_2$—Al$_2$O$_3$—MgO support from Example 1. The support thus obtained, having a dry appearance, was dried in a thin layer in a drying cabinet at 105° C. for 10 h, then finely crushed with a mortar and pestle and heated in a thin layer in a Naber oven to 300° C. within 2 h, kept at 300° C. for 3 h, heated to 600° C. within a further 2 h and finally kept at 600° C. for 3 h.

Example 11

A suspension of 10 g of the cobalt-doped SiO$_2$—Al$_2$O$_3$—MgO support from Example 8 in 33.3 g of demineralized water is heated to 90° C. and stirred at this temperature for 15 min. Added to this suspension while stirring is a solution, heated to 90° C. beforehand, of HAuCl$_4$*3H$_2$O (205 mg) in 8.3 g of water. After the addition, the mixture was stirred for a further 30 min, then cooled, filtered at room temperature, and subsequently washed six times with 50 ml each time of water. The material was dried at 105° C. for 10 h, finely crushed with a mortar and pestle, then heated from 18° C. up to 450° C. within 1 h and calcined at 450° C. for 5 h.

A line scan SEM-EDX analysis of a cut section of catalyst particles embedded into polymer matrix showed an eggshell distribution for Co and for gold.

Example 12

Zn(NO$_3$)$_2$*6H$_2$O (580 mg, 1.95 mmol) is dissolved in 5 g of demineralized water and the solution is mixed by vigorous agitation with 10 g of an SiO$_2$—Al$_2$O$_3$—MgO support from Example 1. The support thus obtained, having a dry appearance, was dried in a thin layer in a drying cabinet at 105° C. for 10 h, then finely crushed with a mortar and pestle and heated in a thin layer in a Naber oven to 300° C. within 2 h, kept at 300° C. for 3 h, heated to 600° C. within a further 2 h and finally kept at 600° C. for 3 h.

Example 13

A suspension of 10 g of the zinc-doped SiO$_2$—Al$_2$O$_3$—MgO support from Example 12 in 33.3 g of demineralized water is heated to 90° C. and stirred at this temperature for 15 min. Added to this suspension while stirring is a solution, heated to 90° C. beforehand, of HAuCl$_4$*3H$_2$O (205 mg) in 8.3 g of water. After the addition, the mixture was stirred for a further 30 min, then cooled, filtered at room temperature, and subsequently washed six times with 50 ml each time of water. The material was dried at 105° C. for 10 h, finely crushed with a mortar and pestle, then heated from 18° C. up to 450° C. within 1 h and calcined at 450° C. for 5 h.

A line scan SEM-EDX analysis of a cut section of catalyst particles embedded into polymer matrix showed an eggshell distribution for Zn and for gold.

Examples 14 to 21 (Batch Tests for MMA Preparation)

A gold-containing catalyst according to Table 1 (384 mg), methacrolein (1.20 g) and methanol (9.48 g) were stirred for 2 h in an atmosphere of 7% by volume of 02 in N$_2$ at 60° C. and a pressure of 30 bar in a 140 ml steel autoclave with a magnetic stirrer. After 2 h, the mixture was cooled down, degassed, filtered and analysed by means of GC. Each catalyst was tested at least twice under identical conditions; the results of the respective experiments were averaged. The resulting conversion of methacrolein (C(MAL), %), the space-time yield (STY, mol MMA/kg cat h) and the selectivity for MMA (S(MMA), %) for every catalyst tested are collated in Table 1 below.

TABLE 1

| Example | Cat. Ex. | Co (or Zn) Distribution | C(MAL) % | STY, mol MMA/ kg(cat) h | S(MMA) % |
|---|---|---|---|---|---|
| 14 | 4 | eggshell | 67.7 | 13.4 | 94.8 |
| 15 | 5 | eggshell | 64.6 | 12.5 | 94.3 |
| 16 | 6 | eggshell | 64.6 | 12.8 | 96.6 |
| 17 | 7 | eggshell | 59.6 | 11.6 | 95.5 |
| 18 | 8 | eggshell | 56.6 | 10.4 | 91.4 |
| 19 | 9 | eggshell | 56 | 10.6 | 94.3 |
| 20 | 11 | eggshell | 58.7 | 11.9 | 92.3 |
| 21 | 13 | eggshell | 47.1 | 9.9 | 93.5 |

Comparative Example 1

A suspension of 10 g of the doped SiO$_2$—Al$_2$O$_3$—MgO support from Example 1 in 33.3 g of demineralized water is heated to 90° C. and stirred at this temperature for 15 min. Added to this suspension while stirring is a solution, heated to 90° C. beforehand, of $HAuCl_4*3H_2O$ (205 mg) in 8.3 g of water. After the addition, the mixture was stirred for a further 30 min, then cooled, filtered at room temperature, and subsequently washed six times with 50 ml each time of water. The material was dried at 105° C. for 10 h, finely crushed with a mortar and pestle, heated from 18° C. up to 450° C. within 1 h and calcined at 450° C. for 5 h.

Comparative Example 2

A 250 ml beaker is initially charged with 21.35 g of $Mg(NO_3)_2*6H_2O$, 31.21 g of $Al(NO_3)_3*9H_2O$ and 4.72 g of $Co(NO_3)_2*6H_2O$ together, which are dissolved in 41.85 g of demineralized water while stirring on a magnetic stirrer. Thereafter, 1.57 g of 60% $HNO_3$ are added while stirring. 166.67 g of silica sol (Köstrosol 1530AS from Bad Köstritz) are weighed into a 500 ml three-neck flask and cooled to 15° C. while stirring. 2.57 g of 60% $HNO_3$ are additionally added gradually to the sol while stirring. At 15° C., the nitrate solution is added to the sol within 45 min while stirring. After the addition, the mixture is heated to 50° C. within 30 min and stirred at this temperature for a further 24 h. After this time, the mixture is dried in a spray drier with an exit temperature of 120° C. The dried powder is heated in a thin layer in a Naber oven to 300° C. over the course of 2 h, kept at 300° C. for 3 h, heated to 600° C. within a further 2 h and finally kept at 600° C. for a further 3 h. The resulting material consisted of round particles having an average particle size of about 60 μm.

Comparative Example 3

A suspension of 10 g of cobalt-doped $SiO_2$—$Al_2O_3$—MgO support from CE2 in 33.3 g of demineralized water is heated to 90° C. and stirred at this temperature for 15 min. Added to this suspension while stirring is a solution, heated to 90° C. beforehand, of $HAuCl_4*3H_2O$ (205 mg) in 8.3 g of water. After the addition, the mixture was stirred for a further 30 min, then cooled, filtered at room temperature, and subsequently washed six times with 50 ml each time of water. The material was dried at 105° C. for 10 h, finely crushed with a mortar and pestle, then heated from 18° C. up to 450° C. within 1 h and calcined at 450° C. for 5 h.

A line scan SEM-EDX analysis of a cut section of catalyst particles embedded in the polymer matrix showed a homogeneous distribution of Co and a poorly defined inhomogeneous distribution for gold.

Comparative Example 4

A suspension of 10 g of the $SiO_2$—$Al_2O_3$—MgO support from Example 1 in 33.3 g of demineralized water is heated to 90° C. and stirred at this temperature for 15 min. Added to this suspension while stirring is a solution, heated to 90° C. beforehand, of $HAuCl_4*3H_2O$ (205 mg) and $Ni(NO_3)_2*6H_2O$ (567 mg, 1.95 mmol) in 8.3 g of water. After the addition, the mixture was stirred for a further 30 min, then cooled, filtered at room temperature, and subsequently washed six times with 50 ml each time of water. The material was dried at 105° C. for 10 h, finely crushed with a mortar and pestle, then heated from 18° C. up to 450° C. within 1 h and calcined at 450° C. for 5 h.

A line scan SEM-EDX analysis of a cut section of catalyst particles embedded into polymer matrix showed an eggshell distribution for Ni and for gold.

Comparative Example 5

A suspension of 10 g of the $SiO_2$—$Al_2O_3$—MgO support from Example 1 in 33.3 g of demineralized water is heated to 90° C. and stirred at this temperature for 15 min. Added to this suspension while stirring is a solution, heated to 90° C. beforehand, of $HAuCl_4*3H_2O$ (205 mg) and $Co(NO_3)_2*6H_2O$ (569 mg, 1.95 mmol) in 8.3 g of water. After the addition, the mixture was stirred for a further 30 min, then cooled, filtered at room temperature, and subsequently washed six times with 50 ml each time of water. The material was dried at 105° C. for 10 h, finely crushed with a mortar and pestle, heated from 18° C. up to 450° C. within 1 h and calcined at 450° C. for 5 h.

Comparative Example 6

A suspension of 10 g of the $SiO_2$—$Al_2O_3$—MgO support from Example 1 in 33.3 g of demineralized water is heated to 90° C. and stirred at this temperature for 15 min. Added to this suspension while stirring is a solution, brought to 90° C. beforehand, of $Co(NO_3)_2*6H_2O$ (569 mg, 1.95 mmol) in 4.2 g of water. After the addition, the mixture is stirred at 90° C. for a further 30 min. Added to this suspension with stirring is a solution, brought to 90° C. beforehand, of $HAuCl_4*3H_2O$ (205 mg) in 4.2 g of water. After the addition, the mixture was stirred at 90° C. for a further 30 min, then cooled down, filtered at room temperature and subsequently washed six times with 50 ml each time of water. The material was dried at 105° C. for 10 h, finely crushed with a mortar and pestle, heated from 18° C. up to 450° C. within 1 h and calcined at 450° C. for 5 h.

Comparative Example 7

A suspension of 10 g of the $SiO_2$—$Al_2O_3$—MgO support from Example 1 in 33.3 g of demineralized water is heated to 90° C. and stirred at this temperature for 15 min. Added to this suspension while stirring is a solution, heated to 90° C. beforehand, of $HAuCl_4*3H_2O$ (205 mg) in 4.2 g of water. After the addition, the mixture was stirred at 90° C. for a further 30 min. Added to this suspension while stirring is a solution, heated to 90° C. beforehand, of $Co(NO_3)_2*6H_2O$ (569 mg, 1.95 mmol) in 4.2 g of water. After the addition, the mixture was stirred at 90° C. for a further 30 min, then cooled down, filtered at room temperature and subsequently washed six times with 50 ml each time of water. The material was dried at 105° C. for 10 h, finely crushed with a mortar and pestle, heated from 18° C. up to 450° C. in 1 h and calcined at 450° C. for 5 h.

Comparative Experiments CE8 to CE13

TABLE 2

Batch tests with catalysts CE1, CE3 to CE7

| Example | Cat. Ex. | Co (or Ni) Distribution | C(MAL), % | STY, mol MMA/ kg(cat) h | S(MMA), % |
|---|---|---|---|---|---|
| CE8 | CE1 | — | 39 | 7.9 | 91.8 |
| CE9 | CE3 | homogeneous | 42 | 8.5 | 91.6 |
| CE10 | CE4 | eggshell | 75.6 | 15.5 | 94.2 |
| CE11 | CE5 | | 6.5 | 1.2 | 86.2 |
| CE12 | CE6 | | 55.9 | 10.9 | 89.1 |
| CE13 | CE7 | | 13.8 | 2.3 | 76.1 |

Continuous Test for Preparation of MMA (General Description)

The pH of a 42.5% by weight solution of MAL in methanol is adjusted to pH=7 while stirring by the addition of a one percent by weight solution of NaOH in methanol. This solution is fed continuously at a constant rate of addition to a stirred and sparged stirred tank reactor (sparging with air) under pressure of 10 bar and at internal temperature of 80° C. At the same time, this reactor containing 20 g of powder catalyst is fed with a sufficient amount of one percent by weight NaOH solution (in methanol) that the value pH=7 in the reactor remains constant. The reaction mixture was withdrawn continuously from the reactor via a filter. After the time specified below, the product samples were taken and analysed by means of GC.

TABLE 3

Continuous tests for MMA preparation with selected catalysts

| Example Cat. | TOS [h] | C (MAL), % | STY, mol MMA/ kg (cat) h | S (MMA), % | D50, µm Fresh cat. | D50, µm Used cat. |
|---|---|---|---|---|---|---|
| 4 | 100 | 75.2 | 12.4 | 95.8 | | |
| 4 | 2000 | 73.8 | 12.2 | 95.5 | 55.6 | 55.2 |
| CE4 | 100 | 77.6 | 10.4 | 96.1 | | |
| CE4 | 2000 | 69.7 | 9.3 | 91.5 | 55.2 | 4.6 |

The examples, especially according to the results in Table 3, show that the catalysts of the invention, compared to the prior art, given identical initial activity and selectivity, have much longer service lives than the prior art catalysts.

THE FIGURES

FIG. 1 shows the distribution of gold (dotted line) and of cobalt (solid line) of a ground catalyst particle from Example 4. The higher concentration of both metals in the respective outer regions of the particles is apparent. The steep rise in the curve at the outermost edges can be explained by a non-smooth surface of the particle.

Figure 2:
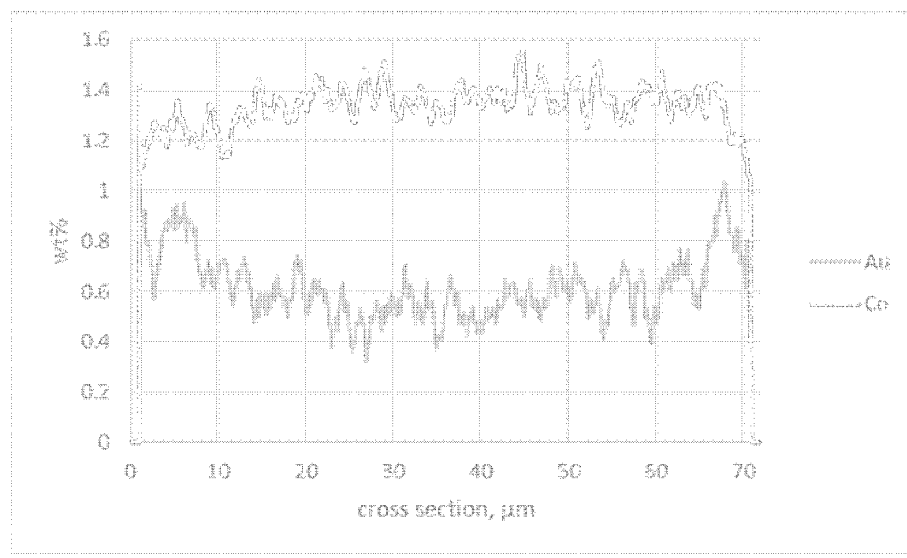

FIG. 2 shows the distribution of gold (dotted line) and of cobalt (solid line) of a ground catalyst particle from Comparative Example 3. The uniform concentration of both metals over the entire particle is apparent. The steep rise in the curve at the outermost edges can be explained by a non-smooth surface of the particle.

Figure 3:
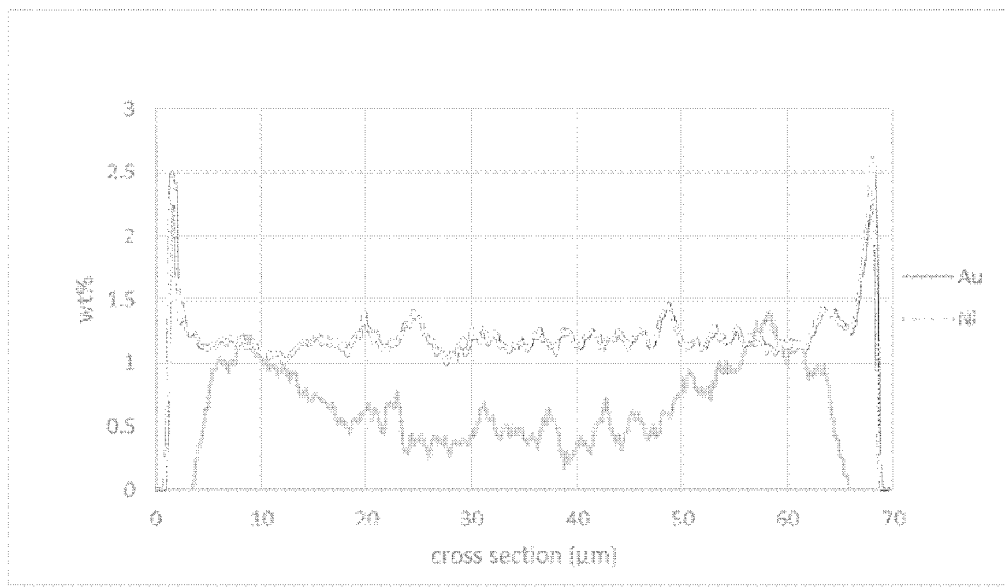

FIG. 3 shows the distribution of gold (dotted line) and of nickel (solid line) of a ground catalyst particle from Comparative Example 4. The higher concentration of both metals in the respective outer regions of the particles is apparent. The steep rise in the curve at the outermost edges can be explained by a non-smooth surface of the particle.

The invention claimed is:

1. A catalyst particle; comprising:
   oxygen;
   silicon;
   aluminum;
   a basic element;
   gold; and
   iron, zinc, and/or cobalt,
   wherein a maximum gold concentration or a maximum iron, zinc and/or cobalt concentration of the catalyst particle in an outer region which makes up a maximum of 60% of a geometric equivalent diameter is at least 1.5 times as high as a gold concentration or iron, zinc or cobalt concentration in a middle region which makes up the remaining region of the geometric equivalent diameter.

2. The catalyst particle according to claim 1, wherein the particle comprises oxygen, silicon, aluminum, a basic element, gold and cobalt.

3. The catalyst particle according to claim 1, wherein the basic element is an alkali metal, an alkaline-earth metal, a rare-earth metal or a mixture of one or more of these metals.

4. The catalyst particle according to claim 1, wherein the catalyst particle comprises, based on the total molar amount of gold, silicon, aluminum and basic elements, and iron, zinc and/or cobalt, 0.03 to 3 mol % of gold, 40 to 90 mol % of silicon, 3 to 40 mol % of aluminum, 2 to 40 mol % of the basic element and 0.1 to 20 mol % of iron, zinc and/or cobalt, where the molar ratio of iron, zinc and/or cobalt to gold is between 0.1 and 20 and all these elements except for the gold are present in the form of oxides.

5. The catalyst particle according to claim 1, wherein the catalyst particle has a mean geometric equivalent diameter between 10 and 250 µm, and the thickness of the outer region is between 2 and 100 sm.

6. The catalyst particle according to claim 1, wherein gold and/or gold- and iron-, zinc- and/or cobalt oxide-containing particles have a mean diameter between 2 and 10 nm and are present in the outer region of the catalyst particle.

7. The catalyst particle according to claim 1, wherein the particles are porous and have a specific surface area between 100 and 300 $m^2/g$, and an average pore diameter thereof is 1 to 50 nm.

8. The catalyst particle according to claim 7, wherein the specific surface area of the catalyst particle is between 150 and 250 $m^2/g$, and the average pore diameter is 2 to 20 nm.

9. The catalyst particle according to claim 1, wherein a thickness of the outer region is between 2 and 100 µm.

10. A process for producing a catalyst particle according to claim 1, comprising:
   1) applying at least one iron, zinc and/or cobalt compound to a particle comprising an oxide of silicon, of aluminum and optionally of one or more alkali metals, alkaline-earth metals or rare-earth metals,
   2) optionally partly or fully oxidizing the material from 1) and optionally drying/calcining,
   3) applying at least one gold compound to the material from 2) and
   4) drying or calcining the material from 3).

11. The process according to claim 10, wherein a cobalt compound is applied in 1).

12. The process according to claim 10, wherein 2) comprises heating in the presence of oxygen or the addition of an oxidizing agent to an aqueous suspension of the particle from 1).

13. The process according to claim 12, wherein 2) comprises a calcination in the presence of oxygen.

14. The process according to claim 10, wherein the particle comprising the oxides of silicon, of aluminum and optionally of one or more alkali metals, alkaline-earth metals or rare-earth metals goes through at least one thermal treatment with water within 1) to 3), the water temperature being between 50 and 100° C.

15. The process according to claim 14, wherein the water temperature is between 70 and 95° C.

16. The process according to claim 10, wherein 1), 3), and optionally 2) are conducted in an aqueous medium, and 1) and 3) are effected using a water-soluble cobalt compound or a water-soluble gold compound.

17. The process according to claim 10, wherein in 3), first a basic solution and then a solution comprising auric acid, having a pH between 0.5 and 5, are added to an aqueous suspension of the particles from 2).

18. The process according to claim 10, wherein in 3), a solution which has been obtained by the partial or complete neutralization of an auric acid solution, having a pH between 0.5 and 5, with a base is added to an aqueous suspension of the particles from 2).

19. A process for producing a carboxylic ester, comprising oxidatively esterifying an aldehyde in the presence of oxygen, an alcohol, and the catalyst particle according to claim 1, to obtain a carboxylic ester.

20. The process of claim 19, wherein the aldehyde is methacrolein and the obtained carboxylic ester is an alkyl methacrylate.

* * * * *